(12) United States Patent
Sasada et al.

(10) Patent No.: US 9,505,824 B2
(45) Date of Patent: Nov. 29, 2016

(54) ANTIGEN PEPTIDE DERIVED FROM THE SEQUENCE OF EPIDERMAL GROWTH FACTOR RECEPTOR HAVING T790M POINT MUTATION

(71) Applicant: Kanagawa Prefectural Hospital Organization, Yokohama-shi, Kanagawa (JP)

(72) Inventors: Tetsuro Sasada, Yokohama (JP); Tetsuya Nakatsura, Kashiwa (JP); Kazuya Ofuji, Kashiwa (JP)

(73) Assignee: Kanagawa Prefectural Hospital Organization, Kanagawa (JP)

( * ) Notice: Subject to any disclaimer, the term of this patent is extended or adjusted under 35 U.S.C. 154(b) by 0 days.

(21) Appl. No.: 14/420,561

(22) PCT Filed: Aug. 8, 2013

(86) PCT No.: PCT/JP2013/071499
§ 371 (c)(1),
(2) Date: Feb. 9, 2015

(87) PCT Pub. No.: WO2014/024965
PCT Pub. Date: Feb. 13, 2014

(65) Prior Publication Data
US 2015/0218248 A1 Aug. 6, 2015

(30) Foreign Application Priority Data
Aug. 10, 2012 (JP) .................................. 2012-177631

(51) Int. Cl.
*A61K 39/00* (2006.01)
*C07K 14/71* (2006.01)
*C07K 4/12* (2006.01)
*C07K 7/06* (2006.01)

(52) U.S. Cl.
CPC ........... *C07K 14/71* (2013.01); *A61K 39/0011* (2013.01); *C07K 4/12* (2013.01); *C07K 7/06* (2013.01); *A61K 2039/572* (2013.01)

(58) Field of Classification Search
None
See application file for complete search history.

(56) References Cited

U.S. PATENT DOCUMENTS

2010/0166744 A1 7/2010 Wong

FOREIGN PATENT DOCUMENTS

| EP | 1712620 A1 | 10/2006 |
| JP | 2010-516770 A | 5/2010 |
| WO | 2013/036201 A1 | 3/2013 |

OTHER PUBLICATIONS

Filho et al., "Novel Immunogenic HLA-A*0201-restricted Epidermal Growth Factor Receptor-specific T-cell Epitope in Head and Neck Cancer Patients," Journal of Immunotherapy, 33: 83-91 (2010).
Shomura et al., "Identification of epidermal growth factor receptor-derived peptides recognised by both cellular and humoral immune responses in HLA-A24+ non-small cell lung cancer patients," European Journal of Cancer, 40: 1776-1786 (2004).
Kosaka et al., "Analysis of Epidermal Growth Factor Receptor Gene Mutation in Patients with Non-Small Cell Lung Cancer and Acquired Resistance to Gefitinib," Clinical Cancer Research, 12: 5764-5769 (2006).
Shomura et al., "Identification of epidermal growth factor receptor-derived peptides recognized by both cellular and humoral immunities in cancer patients," Proceedings of the Japanese Cancer Association, 63: 297 (P-0746) (2004).
Kiura et al., "Hishosaibo Haigan: Shindan to Chiryo no Saizensen Johi Seicho Inshi Juyotai Tyrosine Kinase Sogaiyaku (EGFR-TKIs) no Kanjusei to Taisei (Kobetsuka Chiryo no Kakuritsu ni Mukete)," Mebio, 25: 84-95 (2008).
Harada et al., "HLA-restricted cancer-specific killer T cells," Japanese Journal of Clinical Medicine, 63, special extra issue 4, pp. 579-584, Rinsho Men'ekigaku (first volume)—Kiso Kenkyu no Shinpo to Saishin no Rinsho—(2005).

*Primary Examiner* — Marianne P Allen
(74) *Attorney, Agent, or Firm* — Morgan, Lewis & Bockius LLP

(57) ABSTRACT

The present application relates to an antigen peptide derived from the sequence of epidermal growth factor receptor having T790M point mutation and a pharmaceutical composition for the treatment of cancer comprising the peptide.

10 Claims, 11 Drawing Sheets

SEQUENCE LISTING

```
<160> NUMBER OF SEQ ID NOS: 17

<210> SEQ ID NO 1
<211> LENGTH: 10
<212> TYPE: PRT
<213> ORGANISM: Artificial
<220> FEATURE:
<223> OTHER INFORMATION: Synthetic peptide

<400> SEQUENCE: 1
```

Val Gln Leu Ile Met Gln Leu Met Pro Phe
1               5                   10

<210> SEQ ID NO 2
<211> LENGTH: 10
<212> TYPE: PRT
<213> ORGANISM: Artificial
<220> FEATURE:
<223> OTHER INFORMATION: Synthetic peptide

<400> SEQUENCE: 2

Gln Leu Ile Met Gln Leu Met Pro Phe Gly
1               5                   10

<210> SEQ ID NO 3
<211> LENGTH: 10
<212> TYPE: PRT
<213> ORGANISM: Artificial
<220> FEATURE:
<223> OTHER INFORMATION: Synthetic peptide

<400> SEQUENCE: 3

Leu Ile Met Gln Leu Met Pro Phe Gly Cys
1               5                   10

<210> SEQ ID NO 4
<211> LENGTH: 10
<212> TYPE: PRT
<213> ORGANISM: Artificial
<220> FEATURE:
<223> OTHER INFORMATION: Synthetic peptide

<400> SEQUENCE: 4

Ile Met Gln Leu Met Pro Phe Gly Cys Leu
1               5                   10

<210> SEQ ID NO 5
<211> LENGTH: 10
<212> TYPE: PRT
<213> ORGANISM: Artificial
<220> FEATURE:
<223> OTHER INFORMATION: Synthetic peptide

<400> SEQUENCE: 5

Met Gln Leu Met Pro Phe Gly Cys Leu Leu
1               5                   10

<210> SEQ ID NO 6
<211> LENGTH: 11
<212> TYPE: PRT
<213> ORGANISM: Artificial
<220> FEATURE:
<223> OTHER INFORMATION: Synthetic peptide

<400> SEQUENCE: 6

Leu Thr Ser Thr Val Gln Leu Ile Met Gln Leu
1               5                   10

<210> SEQ ID NO 7
<211> LENGTH: 11
<212> TYPE: PRT
<213> ORGANISM: Artificial
<220> FEATURE:
<223> OTHER INFORMATION: Synthetic peptide

<400> SEQUENCE: 7

Leu Ile Met Gln Leu Met Pro Phe Gly Cys Leu

<210> SEQ ID NO 8
<211> LENGTH: 11
<212> TYPE: PRT
<213> ORGANISM: Artificial
<220> FEATURE:
<223> OTHER INFORMATION: Synthetic peptide

<400> SEQUENCE: 8

```
Ile Met Gln Leu Met Pro Phe Gly Cys Leu Leu
1               5                   10
```

<210> SEQ ID NO 9
<211> LENGTH: 9
<212> TYPE: PRT
<213> ORGANISM: Artificial
<220> FEATURE:
<223> OTHER INFORMATION: Synthetic peptide

<400> SEQUENCE: 9

```
Gly Ile Leu Gly Phe Val Phe Thr Leu
1               5
```

<210> SEQ ID NO 10
<211> LENGTH: 9
<212> TYPE: PRT
<213> ORGANISM: Artificial
<220> FEATURE:
<223> OTHER INFORMATION: Synthetic peptide

<400> SEQUENCE: 10

```
Ser Leu Tyr Asn Thr Val Ala Thr Leu
1               5
```

<210> SEQ ID NO 11
<211> LENGTH: 1210
<212> TYPE: PRT
<213> ORGANISM: homo sapiens

<400> SEQUENCE: 11

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
                20                  25                  30

Gly Thr Ser Asn Lys Leu Thr Gln Leu Gly Thr Phe Glu Asp His Phe
            35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
                100                 105                 110

Tyr Glu Asn Ser Tyr Ala Leu Ala Val Leu Ser Asn Tyr Asp Ala Asn
            115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160
```

-continued

```
Ser Ile Gln Trp Arg Asp Ile Val Ser Ser Asp Phe Leu Ser Asn Met
                165                 170                 175
Ser Met Asp Phe Gln Asn His Leu Gly Ser Cys Gln Lys Cys Asp Pro
            180                 185                 190
Ser Cys Pro Asn Gly Ser Cys Trp Gly Ala Gly Glu Glu Asn Cys Gln
        195                 200                 205
Lys Leu Thr Lys Ile Ile Cys Ala Gln Gln Cys Ser Gly Arg Cys Arg
    210                 215                 220
Gly Lys Ser Pro Ser Asp Cys Cys His Asn Gln Cys Ala Ala Gly Cys
225                 230                 235                 240
Thr Gly Pro Arg Glu Ser Asp Cys Leu Val Cys Arg Lys Phe Arg Asp
                245                 250                 255
Glu Ala Thr Cys Lys Asp Thr Cys Pro Pro Leu Met Leu Tyr Asn Pro
            260                 265                 270
Thr Thr Tyr Gln Met Asp Val Asn Pro Glu Gly Lys Tyr Ser Phe Gly
        275                 280                 285
Ala Thr Cys Val Lys Lys Cys Pro Arg Asn Tyr Val Val Thr Asp His
    290                 295                 300
Gly Ser Cys Val Arg Ala Cys Gly Ala Asp Ser Tyr Glu Met Glu Glu
305                 310                 315                 320
Asp Gly Val Arg Lys Cys Lys Lys Cys Glu Gly Pro Cys Arg Lys Val
                325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
        355                 360                 365
Leu His Ile Leu Pro Val Ala Phe Arg Gly Asp Ser Phe Thr His Thr
    370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
                405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
                485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
        515                 520                 525
Val Ser Arg Gly Arg Glu Cys Val Asp Lys Cys Asn Leu Leu Glu Gly
    530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
                565                 570                 575
Asp Asn Cys Ile Gln Cys Ala His Tyr Ile Asp Gly Pro His Cys Val
```

```
            580                 585                 590
Lys Thr Cys Pro Ala Val Met Gly Glu Asn Asn Thr Leu Val Trp
            595                 600                 605
Lys Tyr Ala Asp Ala Gly His Val Cys His Leu Cys His Pro Asn Cys
        610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Thr Gly Met Val Gly Ala Leu Leu Leu
                645                 650                 655
Leu Leu Val Val Ala Leu Gly Ile Gly Leu Phe Met Arg Arg Arg His
                660                 665                 670
Ile Val Arg Lys Arg Thr Leu Arg Arg Leu Leu Gln Glu Arg Glu Leu
            675                 680                 685
Val Glu Pro Leu Thr Pro Ser Gly Glu Ala Pro Asn Gln Ala Leu Leu
            690                 695                 700
Arg Ile Leu Lys Glu Thr Glu Phe Lys Lys Ile Lys Val Leu Gly Ser
705                 710                 715                 720
Gly Ala Phe Gly Thr Val Tyr Lys Gly Leu Trp Ile Pro Glu Gly Glu
                725                 730                 735
Lys Val Lys Ile Pro Val Ala Ile Lys Glu Leu Arg Glu Ala Thr Ser
                740                 745                 750
Pro Lys Ala Asn Lys Glu Ile Leu Asp Glu Ala Tyr Val Met Ala Ser
            755                 760                 765
Val Asp Asn Pro His Val Cys Arg Leu Leu Gly Ile Cys Leu Thr Ser
770                 775                 780
Thr Val Gln Leu Ile Met Gln Leu Met Pro Phe Gly Cys Leu Leu Asp
785                 790                 795                 800
Tyr Val Arg Glu His Lys Asp Asn Ile Gly Ser Gln Tyr Leu Leu Asn
                805                 810                 815
Trp Cys Val Gln Ile Ala Lys Gly Met Asn Tyr Leu Glu Asp Arg Arg
                820                 825                 830
Leu Val His Arg Asp Leu Ala Ala Arg Asn Val Leu Val Lys Thr Pro
            835                 840                 845
Gln His Val Lys Ile Thr Asp Phe Gly Leu Ala Lys Leu Leu Gly Ala
            850                 855                 860
Glu Glu Lys Glu Tyr His Ala Glu Gly Gly Lys Val Pro Ile Lys Trp
865                 870                 875                 880
Met Ala Leu Glu Ser Ile Leu His Arg Ile Tyr Thr His Gln Ser Asp
                885                 890                 895
Val Trp Ser Tyr Gly Val Thr Val Trp Glu Leu Met Thr Phe Gly Ser
            900                 905                 910
Lys Pro Tyr Asp Gly Ile Pro Ala Ser Glu Ile Ser Ser Ile Leu Glu
            915                 920                 925
Lys Gly Glu Arg Leu Pro Gln Pro Pro Ile Cys Thr Ile Asp Val Tyr
930                 935                 940
Met Ile Met Val Lys Cys Trp Met Ile Asp Ala Asp Ser Arg Pro Lys
945                 950                 955                 960
Phe Arg Glu Leu Ile Ile Glu Phe Ser Lys Met Ala Arg Asp Pro Gln
                965                 970                 975
Arg Tyr Leu Val Ile Gln Gly Asp Glu Arg Met His Leu Pro Ser Pro
            980                 985                 990
Thr Asp Ser Asn Phe Tyr Arg Ala  Leu Met Asp Glu Glu  Asp Met Asp
            995                 1000                1005
```

Asp Val Val Asp Ala Asp Glu Tyr Leu Ile Pro Gln Gln Gly Phe
    1010                1015                1020

Phe Ser Ser Pro Ser Thr Ser Arg Thr Pro Leu Leu Ser Ser Leu
    1025                1030                1035

Ser Ala Thr Ser Asn Asn Ser Thr Val Ala Cys Ile Asp Arg Asn
    1040                1045                1050

Gly Leu Gln Ser Cys Pro Ile Lys Glu Asp Ser Phe Leu Gln Arg
    1055                1060                1065

Tyr Ser Ser Asp Pro Thr Gly Ala Leu Thr Glu Asp Ser Ile Asp
    1070                1075                1080

Asp Thr Phe Leu Pro Val Pro Glu Tyr Ile Asn Gln Ser Val Pro
    1085                1090                1095

Lys Arg Pro Ala Gly Ser Val Gln Asn Pro Val Tyr His Asn Gln
    1100                1105                1110

Pro Leu Asn Pro Ala Pro Ser Arg Asp Pro His Tyr Gln Asp Pro
    1115                1120                1125

His Ser Thr Ala Val Gly Asn Pro Glu Tyr Leu Asn Thr Val Gln
    1130                1135                1140

Pro Thr Cys Val Asn Ser Thr Phe Asp Ser Pro Ala His Trp Ala
    1145                1150                1155

Gln Lys Gly Ser His Gln Ile Ser Leu Asp Asn Pro Asp Tyr Gln
    1160                1165                1170

Gln Asp Phe Phe Pro Lys Glu Ala Lys Pro Asn Gly Ile Phe Lys
    1175                1180                1185

Gly Ser Thr Ala Glu Asn Ala Glu Tyr Leu Arg Val Ala Pro Gln
    1190                1195                1200

Ser Ser Glu Phe Ile Gly Ala
    1205            1210

<210> SEQ ID NO 12
<211> LENGTH: 10
<212> TYPE: PRT
<213> ORGANISM: Artificial
<220> FEATURE:
<223> OTHER INFORMATION: Synthetic peptide

<400> SEQUENCE: 12

Thr Gln Leu Met Pro Phe Gly Cys Leu Leu
1               5                   10

<210> SEQ ID NO 13
<211> LENGTH: 9
<212> TYPE: PRT
<213> ORGANISM: Artificial
<220> FEATURE:
<223> OTHER INFORMATION: Synthetic peptide

<400> SEQUENCE: 13

Asn Leu Val Pro Met Val Ala Thr Val
1               5

<210> SEQ ID NO 14
<211> LENGTH: 8
<212> TYPE: PRT
<213> ORGANISM: Artificial
<220> FEATURE:
<223> OTHER INFORMATION: Synthetic peptide

<400> SEQUENCE: 14

```
Ser Ile Ile Asn Phe Glu Lys Leu
1               5

<210> SEQ ID NO 15
<211> LENGTH: 9
<212> TYPE: PRT
<213> ORGANISM: Artificial
<220> FEATURE:
<223> OTHER INFORMATION: Synthetic peptide

<400> SEQUENCE: 15

Ile Met Gln Leu Met Pro Phe Gly Cys
1               5

<210> SEQ ID NO 16
<211> LENGTH: 9
<212> TYPE: PRT
<213> ORGANISM: Artificial
<220> FEATURE:
<223> OTHER INFORMATION: Synthetic peptide

<400> SEQUENCE: 16

Ile Met Gln Leu Met Pro Phe Gly Val
1               5

<210> SEQ ID NO 17
<211> LENGTH: 9
<212> TYPE: PRT
<213> ORGANISM: Artificial
<220> FEATURE:
<223> OTHER INFORMATION: Synthetic peptide

<400> SEQUENCE: 17

Ile Met Gln Leu Met Pro Phe Gly Leu
1               5
```

ANTIGEN PEPTIDE DERIVED FROM THE SEQUENCE OF EPIDERMAL GROWTH FACTOR RECEPTOR HAVING T790M POINT MUTATION

A computer readable text file, entitled "SequenceListing.txt," created on or about Mar. 17, 2015 with a file size of about 14 kb contains the sequence listing for this application and is hereby incorporated by reference in its entirety.

TECHNICAL FIELD

The present application relates to an antigen peptide derived from the sequence of epidermal growth factor receptor having T790M point mutation and a pharmaceutical composition for the treatment of cancer comprising the peptide.

BACKGROUND

Non-small cell lung cancer is a quite common cancer since the annual number of patients and fatalities in Japan are approximately 90,000 (the third largest among malignant cancers) and 65,000 (the leading cause of death among malignant cancers), respectively. Also, the number of patients in the United States and Europe are estimated as 220,000 and 390,000, respectively. The current therapy for non-small cell lung cancer uses an epidermal growth factor receptor (EGFR) tyrosine kinase inhibitor. However, patients having T790M point mutation of EGFR are resistant to the EGFR tyrosine kinase inhibitor. About 20% of advanced-stage patients of non-small cell lung cancer have the T790M point mutation. Therefore, effective therapies for the patients with the EGFR tyrosine kinase inhibitor resistance has been required.

EGFR853-861 has been reported as an HLA-A2-restricted antigen peptide derived from the amino acid sequence of EGFR (Non Patent Document 1). However, the peptide is derived from the amino acid sequence of wild-type EGFR, which is an autoantigen, and thus T cells expressing a T cell receptor with high affinity to the peptide has already disappeared due to the selection in thymus (i.e., immune tolerance). Therefore, the peptide is not expected to have a high immunogenicity.

CITATION LIST

Non Patent Document

Non Patent Document 1: Andrade, et al., Novel immunogenic HLA-A*0201-restricted epidermal growth factor receptor-specific T-cell epitope in head and neck cancer patients. J Immunother. 2010, 83-91 (herein incorporated by reference)

SUMMARY OF INVENTION

An object of the invention is to provide an antigen peptide that is useful to treat cancer patients having T790M point mutation of EGFR.

The present application provides a peptide consisting of 10-30 amino acid residues comprising the amino acid sequence of SEQ ID NO: 5; 11-30 amino acid residues comprising the amino acid sequence of SEQ ID NO: 7; or 9-30 amino acid residues comprising the amino acid sequence of SEQ ID NO: 15 that is derived from the sequence of epidermal growth factor receptor having T790M point mutation, and having an ability to induce peptide-specific cytotoxic T lymphocytes (CTLs). In particular, the present application provides a peptide consisting of the amino acid sequence of SEQ ID NO: 5, 7, or 15.

The present application also provides a pharmaceutical composition for the treatment of cancer comprising the aforementioned peptide.

The peptide of the invention comprises a point mutation involved in malignant alteration of cancer. Therefore, the peptide of the invention is 1) expected to be recognized as a foreign antigen inside the body of a patient and show a high immunogenicity, and 2) not likely to show escape from immunosurveillance caused by loss of vaccine antigen in cancer cells. The present invention provides a novel therapeutic option for cancer patients having T790M point mutation who have not been effectively treated.

DESCRIPTION OF EMBODIMENTS

Figure 1:
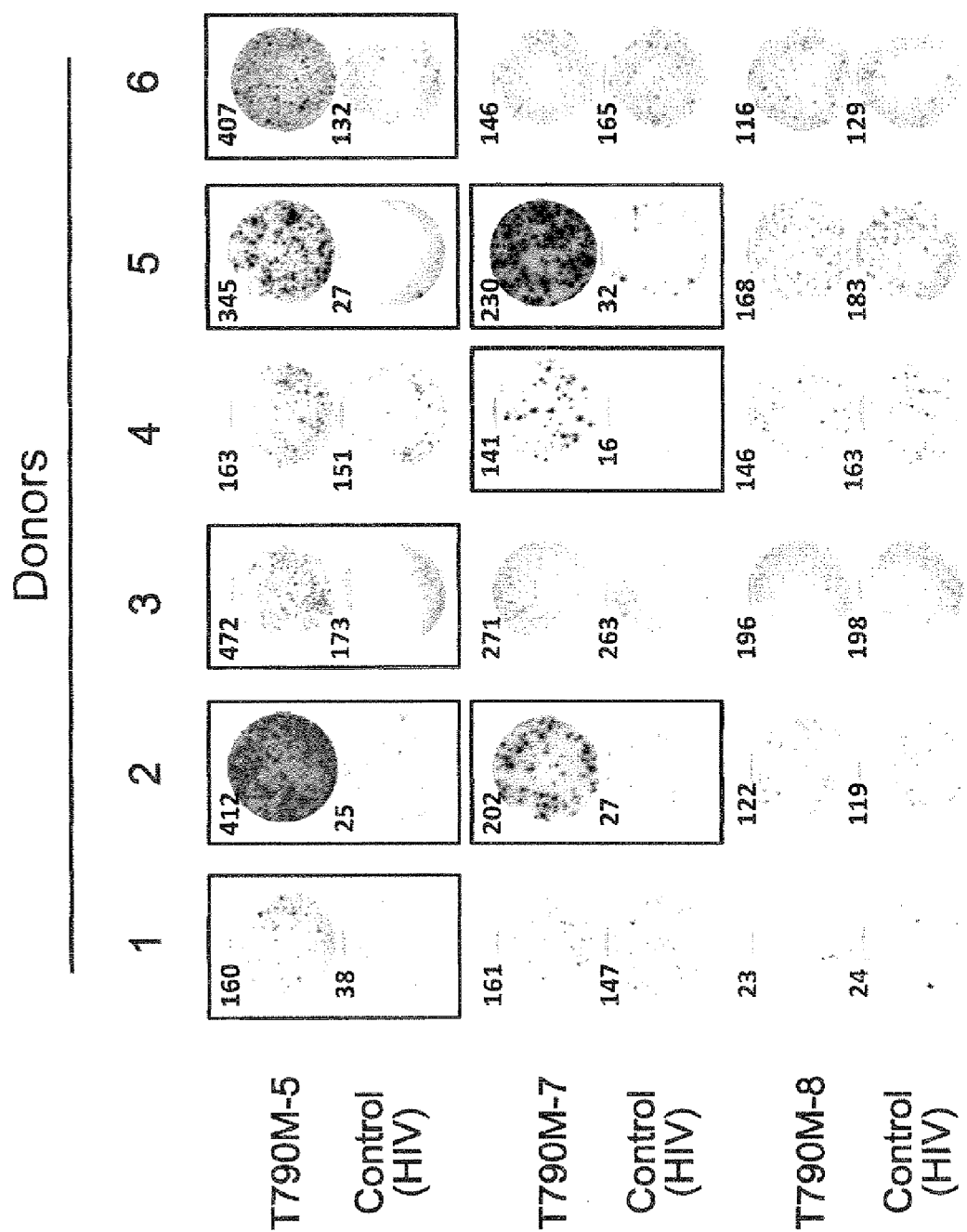
FIG. 1. Immunogenicity of T790M-5 and T790M-7 peptides in peripheral blood mononuclear cells (PBMCs) from normal donors. Immunogenicity of T790M-5 and T790M-7 peptides was examined with PBMCs from 6 different HLA-A2$^+$ healthy donors. PBMCs were stimulated 5 times with T790M-5 or T790M-7 peptide (10 μg/ml) every 3 or 4 days. The stimulated PBMCs (3×10$^4$ cells/well) were examined for reactivity against T2 cells (1×10$^4$ cells/well) pulsed with T790M-5 or T790M-7 or control HIV peptide (10 μg/ml) by IFN-γ ELISPOT assay.

The present application provides a peptide derived from the sequence of epidermal growth factor receptor (EGFR) having T790M point mutation (EGFR-T790M) comprising the amino acid sequence of SEQ ID NO: 5, 7, or 15 and having an ability to induce peptide-specific CTLs. The amino acid sequence of EGFR-T790M is shown in SEQ ID NO: 11. The peptide of the invention may be a peptide that can bind to an HLA molecule by itself, or may be a peptide that produces a peptide comprising the amino acid sequence of SEQ ID NO: 5, 7, or 15 and binding to an HLA molecule when fragmented in a cell. The peptide is preferably, but not limited to, 10-30 amino acids, 11-30 amino acids, or 9-30 amino acids, more preferably 10-15 amino acids, 11-15 amino acids, or 9-15 amino acids in length.

The ability of the peptide to induce peptide-specific CTLs may be examined, for example, by determining a cytokine such as interferon-γ (IFN-γ) produced from PBMCs stimulated with the peptide in response to antigen presenting cells pulsed with the same peptide, by a method such as ELISA or ELISPOT. Alternatively, the ability may be examined by determining cytotoxicity of the induced CTLs by a method such as a ⁵¹Cr-release assay.

In a preferred embodiment, the peptide of the invention is a peptide consisting of the amino acid sequence of SEQ ID NO: 5, 7, or 15.

A constituent amino acid of the peptide of the invention may be a natural amino acid or an amino acid analogue. Examples of the amino acid analogue include N-acylated, O-acylated, esterified, acid amidated and alkylated amino acids. The peptide of the invention may comprise a modification at the constituent amino acid or a moiety such as a carboxylic group, so long as the modification does not significantly deteriorate the function of the peptide. The modification may be addition of formyl, acetyl or t-butoxycarbonyl group at the N-terminus- or free-amino group, or addition of methyl, ethyl, t-butyl or benzyl group at the C-terminus- or free carboxylic group.

The peptide of the invention may be synthesized by a conventionally used peptide synthesizing procedure. Examples of the conventionally used procedure are those described in the literatures including "Peptide Synthesis", Interscience, New York, 1966; "The Proteins", vol. 2, Academic Press Inc., New York, 1976; *"Pepuchido-Gosei"*, Maruzen Co. Ltd., 1975; *"Pepuchido-Gosei-no-Kiso-to-Jikkenn"*, Maruzen Co. Ltd., 1985; and *"Iyakuhin-no-Kaihatu, Zoku*, vol. 14, *Peputido-Gosei"*, Hirokawa Shoten, 1991, (those references are herein incorporated by reference).

The peptide of the invention, when administered to a patient, induces CTLs that recognize a complex of the cancer antigen peptide and an HLA molecule on cancer cells to kill the cells (i.e., cancer-reactive CTLs) inside the body of the patient, and thereby exerts an anti-cancer effect. Therefore, the peptide of the invention may be used as a pharmaceutical composition for the treatment of cancer, such as a cancer vaccine or a CTL inducer.

The pharmaceutical composition of the invention may be used to treat a cancer expressing EGFR-T790M. Preferably, the pharmaceutical composition of the invention is used to treat non-small cell lung cancer.

As used herein, the treatment of cancer includes both prophylactic and therapeutic treatments. The treatment of cancer includes, for example, tumor shrinkage or suppression of tumor growth, suppression of tumorous lesion appearance, prolonged survival, improvement or suppression of exacerbation of a subjective or objective symptom associated with tumor, suppression of metastasis, and prevention of recurrence.

The pharmaceutical composition of the invention may be administrated intradermally or subcutaneously. The pharmaceutical composition of the invention may comprise a pharmaceutically acceptable salt or carrier suitable for the administration. Examples of the salt may include an alkali metal hydrogencarbonate such as sodium chloride and sodium hydrogen carbonate. Preferably, for administration, the pharmaceutical composition is dissolved in a vehicle such as water to provide a solution isotonic to plasma. Examples of the carrier may include cellulose, amino acid polymers and albumin. The peptide of the invention may be conjugated with the carrier as appropriate.

The pharmaceutical composition of the invention may be formulated as a liposomal preparation, a particulate preparation in which the ingredient is bound to a bead having a diameter of several micro maters, or a preparation in which the ingredient is attached to a lipid. For effective establishment of immunity, the pharmaceutical composition of the invention may be administered along with incomplete Freund's adjuvant (ISA-51 (SEPPIC), for example) or a polysaccharide such as pullulan, which has conventionally been used for vaccination, or an immunopotentiating agent such as complete Freund's adjuvant, Bacillus Calmette-Guérin (BCG), Alum, GM-CSF, IL-2, and CpG.

The dosage of the pharmaceutical composition of the invention may be determined as appropriate based on a factor such as condition of the disease to be treated, or age or body weight of the patient to be treated. In general, the amount of the peptide in the pharmaceutical composition to be administered may be 0.0001 to 1000 mg, preferably 0.001 to 100 mg, more preferably 0.01 to 10 mg, still more preferably 0.1 to 5 mg or 0.5 to 3 mg per administration.

Preferably, the pharmaceutical composition may be repeatedly administered once every several days, several weeks or several months.

The peptide of the invention may be used to induce cancer-reactive CTLs in vitro. Therefore, the present application provides a method for inducing cancer-reactive CTLs comprising the step of contacting the peptide of the invention with PBMCs collected from a patient. The CTLs may be induced, for example, by incubating PBMCs collected from a patient in vitro in the presence of the peptide of the invention. The method for inducing cancer-reactive CTLs is useful for adoptive immunotherapy, wherein CTLs induced from PBMCs of a patient are returned into the patient to kill cancer cells.

The peptide of the invention also may be used to prepare antigen presenting cells that induce cancer-reactive CTLs in a cancer patient. Therefore, the present application provides a method for preparing antigen presenting cells comprising the step of contacting the peptide of the invention with cells having antigen-presenting ability collected from a patient. The antigen presenting cells may be prepared by culturing cells having antigen-presenting ability collected from a patient in the presence of the peptide of the invention such that the peptide is bound to and presented on an HLA molecule. Alternatively, the antigen presenting cells may be prepared by introducing a vector being able to express the peptide into cells having antigen-presenting ability collected from a patient such that the peptide is expressed in the cells. Examples of the cells having antigen presenting ability include dendritic cells. Dendritic cells derived from a patient may be prepared from PBMCs collected from a patient by isolating cells adhered to the culture plate of the PBMC culture and then, incubating the isolated cells in the presence of IL-4 and GM-CSF for one week. The antigen presenting cells prepared by the method can induce CTLs that specifically recognize a complex between the peptide and an HLA molecule presented on the surface of cancer cells. When administered to a cancer patient, the antigen presenting cells can promote the induction of cancer-reactive CTLs inside the body of the patient. Accordingly, the antigen presenting cells prepared with the peptide of the invention may be used as a pharmaceutical composition for the treatment of cancer.

The present application provides a nucleic acid molecule encoding the peptide of the invention and a vector comprising the nucleic acid molecule. When introduced into antigen presenting cells, the vector comprising the nucleic acid molecule expresses the peptide of the invention, and then a complex between the expressed peptide and an HLA molecule is presented on the surface of the cells. The antigen presenting cells thus obtained can effectively increase CTLs that kills cancer cells expressing EGFR-T790M.

Examples of vectors in which the nucleic acid molecule of the invention is incorporated may include various plasmid vectors and viral vectors such as adenovirus, adeno-associated virus, retrovirus and vaccinia virus vectors (Liu M, Acres B, Balloul J M, Bizouarne N, Paul S, Slos P, Squiban P. Gene-based vaccines and immunotherapeutics. Proc Natl Acad Sci USA 101 Suppl, 14567-71, 2004, herein incorporated by reference). Methods for preparing the vectors have been well known in the art (Molecular Cloning: A laboratory manual, 2nd ed. New York, Cold Spring Harbor Laboratory, herein incorporated by reference).

The vector of the invention may be administered to a patient so that the peptide of the invention is expressed in antigen presenting cells inside the body of the patient. Alternatively, the vector may be introduced ex vivo into suitable cells, for example dendritic cells derived from a patient, so that the cells express the peptide of the invention, and then the cells thus obtained may be returned to the patient. Those methods are well known in the art (Hrouda D, Dalgleish A G. Gene therapy for prostate cancer. Gene Ther 3: 845-52, 1996, herein incorporated by reference).

When the vector is administered to a patient, the amount of the vector to be administered may vary depending on a factor such as condition of the disease to be treated or age or body weight of the patient to be treated. The vector may be administered 0.1 µg to 100 mg, preferably 1 µg to 50 mg as an amount of DNA. The vector may be administered, for example, intravenously, subcutaneously, or intradermally.

The present invention is further illustrated by the following examples, but is not restricted by these examples in any way.

EXAMPLE 1

1. Materials and Methods (1) Peptides and Cell Lines

The peptides comprising the mutated residue at position 790 (T790M) of EGFR, a wild-type peptide, and control HLA-A2-restricted peptides, influenza $M1_{58-66}$ (Flu-M1, GILGFVFTL) (SEQ ID NO: 9) and HIV-derived peptides (SLYNTVATL) (SEQ ID NO: 10), were provided by Thermo Fisher Scientific GmbH (Bremen, Germany) at the purities of higher than 90%. NSCLC cell lines, NCI-H1975, and HCC827 were obtained from American Type Culture Collection (ATCC; Manassas, Va., USA). NCI-H1975-A2 cells were established by stable transfection with the plasmid carrying HLA-A2 cDNA (pCMV-HLA-A2). These cell lines were maintained in RPMI 1640 medium (Invitrogen, Carlsbad, Calif.) supplemented with 10% heat inactivated fetal bovine serum (FBS), 100 µg/ml streptomycin, and 100 IU/ml penicillin. Expression of HLA-A2 on their cell surface was examined by flow cytometry with anti-HLA-A2 mAb (BB7.2; BD Biosciences, San Jose, Calif.).

(2) Prediction of EGFR-T790M-Derived HLA-A2-Binding Peptides

Two servers, NetMHC 3.2 (http://www.cbs.dtu.dk/services/NetMHC) and BIMAS (http://www-bimas.cit.nih.gov/molbio/hla_bind), were employed to predict 9-mer or 10-mer HLA-A2 binding peptides from EGFR-T790M. For prediction of 11-mer HLA-A2 binding peptides, only NetMHC 3.2 was used. Peptides that showed better scores by either or both of these prediction servers were selected for further evaluation.

(3) HLA Class I Stabilization Assay

The actual binding of predicted peptides to an HLA-A2 molecule was evaluated by MHC class I stabilization assay with TAP2-deficient RMA-S cells stably transfected with the HLA-A2 gene (RMA-S/A2). Briefly, RMA-S/A2 cells were cultured for 18 hours at 26° C. in RPMI 1640 medium in the presence of each synthetic peptide (10 µg/ml) and β2-microglobulin. After washing, the cells were cultured for hours at 37° C., and then stained with anti-HLA-A2 mAb (BB7.2), followed by analysis with flow cytometry. The binding capability of each peptide to an HLA-A2 molecule was evaluated by the increase in mean fluorescence intensity (MFI) of the HLA-A2 expression, as follows: MFI increase (%)=(MFI with a given peptide−MFI without peptide)/(MFI without peptide)×100. The HLA-A2-restricted influenza M1$_{58-66}$ epitope (Flu-M1) was used as a positive control.

(4) Generation of Antigen-Specific T Cells

Peptide-specific T cell lines were generated according to the previously reported method with slight modifications. In brief, peripheral blood was obtained with written informed consent from HLA-A2$^+$ healthy donors and lung cancer patients under the approval of the Institutional Review Board at Kurume University. HLA-A2 expression was confirmed by flow cytometry with anti-HLA-A2 mAb. PBMCs (1×10$^5$ cells/well) purified by Ficoll-Paque density centrifugation were incubated with 10 µg/ml of each peptide in 96 round well plates (Nunc, Roskilde, Denmark) in 200 µl of the culture medium containing 45% RPMI 1640, 45% AIM-V medium (Gibco BRL, Gaithersburg, Md., USA), 10% FCS, 20 IU/ml IL-2, and 0.1 mM MEM nonessential amino-acid solution (Gibco BRL). At every 3 or 4 days, half of the culture medium was removed and replaced by new medium containing the same peptide (10 µg/ml) and 20 IU/ml IL-2. After 14 days of culture, the cells were used for interferon (IFN)-γ ELSPOT or cytotoxicity assays.

(5) Immune Assays

For IFN-γ ELISPOT assay (MBL, Nagoya, Japan), the peptide-stimulated PBMC (3×10$^4$ cells/well) were cultured for 18 hours at 37° C. with T2 cells (1×10$^4$ cells/well) loaded without or with the control or specific peptide (10 µg/ml) in 96-well ELISPOT plate (MultiScreen HTS, Millipore) coated with anti-human IFN-γ mAb. After washing, the spots were developed with biotin-conjugated anti-human IFN-γ mAb, streptavidin-ALP, and BCIP/NBT substrate, in accordance with the manufacturer's instructions. The spot numbers were then counted by an ELISPOT reader (CTL Technologies). The peptide-stimulated PBMCs were also tested for their reactivity against NCI-H1975 (HLA-A2$^-$ T790M$^+$), NCI-H1975-A2 (HLA-A2$^+$ T790M$^+$), and HCC827 (HLA-A2$^-$ T790M$^-$) by IFN-γ ELISPOT assay. In some experiments, CD8$^+$ T cells were isolated using a CD8 Negative Isolation Kit (Miltenyi Biotec) from the peptide-stimulated PBMCs. Anti-HLA class I (W6/32) or anti-HLA class II (L243) antibody was added at 10 µg/ml. The anti-HLA class I (W6/32) and anti-HLA class II (L243) antibodies were obtained by purification of antibodies secreted from hybridoma cells purchased from ATCC.

Peptide-stimulated PBMCs were also tested for cytotoxicity against NCI-H1975 or NCI-H1975-A2 by a standard 6-h $^{51}$Cr-release assay. Two thousand $^{51}$Cr-labelled cells per well were cultured with effector cells in 96-round well plates at the indicated effector/target ratio (ratio of effector cells to target cells). The spontaneous and maximal release was determined by the target cells cultured in medium without or with 1% Triton X-100 (Wako Pure Chemical Industries, Osaka, Japan), respectively. The specific lysis was calculated as follows: specific lysis (%)=[(test release−spontaneous release)/(maximal release−spontaneous release)]×100.

2. Results (1) Prediction of EGFR-T790M-Derived HLA-A2-Binding Peptides

Peptides (9 to 11-mer) that would bind to an HLA-A2 molecule with higher probability were predicted by using NetMHC 3.2 and/or BIMAS servers. Eight peptides that showed better scores by either or both of these prediction servers were selected, and evaluated for the actual binding to the HLA-A2 molecule (Table 1).

TABLE 1

HLA-A2-binding capability of predicted EGFR-T790M-derived peptides.

| Peptide | Amino acid sequence | HLA binding capability (%) |
|---|---|---|
| T790M-1 | VQLIMQLMPF (SEQ ID NO: 1) | 0 |
| T790M-2 | QLIMQLMPFG (SEQ ID NO: 2) | 0 |
| T790M-3 | LIMQLMPFGC (SEQ ID NO: 3) | 0 |
| T790M-4 | IMQLMPFGCL (SEQ ID NO: 4) | 0 |
| T790M-5 | MQLMPFGCLL (SEC) ID NO: 5) | 266.7 |
| T790M-6 | LTSTVQLIMQL (SEQ ID NO: 6) | 0 |
| T790M-7 | LIMQLMPFGCL (SEQ ID NO: 7) | 31.2 |
| T790M-8 | IMQLMPFGCLL (SEQ ID NO: 8) | 69.3 |
| Flu M1 | GILGFVFTL (SEQ ID NO: 9) | 229.1 |

(2) HLA-A2-Binding Capability of EGFR-T790M-Derived Peptides

The HLA-A2-binding capability of the selected peptides was confirmed by cell surface HLA class I stabilization assay with the TAP-deficient cell line RMA-S stably expressing HLA-A2. As illustrated in Table 1, three of the eight selected peptides showed substantial binding to HLA-A2. The binding affinity of T790M-5 to HLA-A2 was much stronger than those of T790M-7 and T790M-8.

(3) Immunogenicity of EGFR-T790M-Derived HLA-A2-Binding Peptides in CD8$^+$ T Cells from Normal Donors To know the immunogenicity of the EGFR-T790M-derived HLA-A2-binding peptides, PBMCs from 6 different HLA-A2$^+$ healthy donors were repeatedly stimulated with the synthetic peptide, T790M-5, T790M-7, or T790M-8. As shown in FIG. 1, after repeated stimulation, T cell lines secreting IFN-γ in response to T790M-5 were established in 5 of 6 healthy donors. Also, after repeated stimulation, T cell lines secreting IFN-γ in response to T790M-7 were established in 3 of 6 healthy donors. However, none of the 6 healthy donors showed antigen-specific T cell response to T790M-8.

Figure 2:
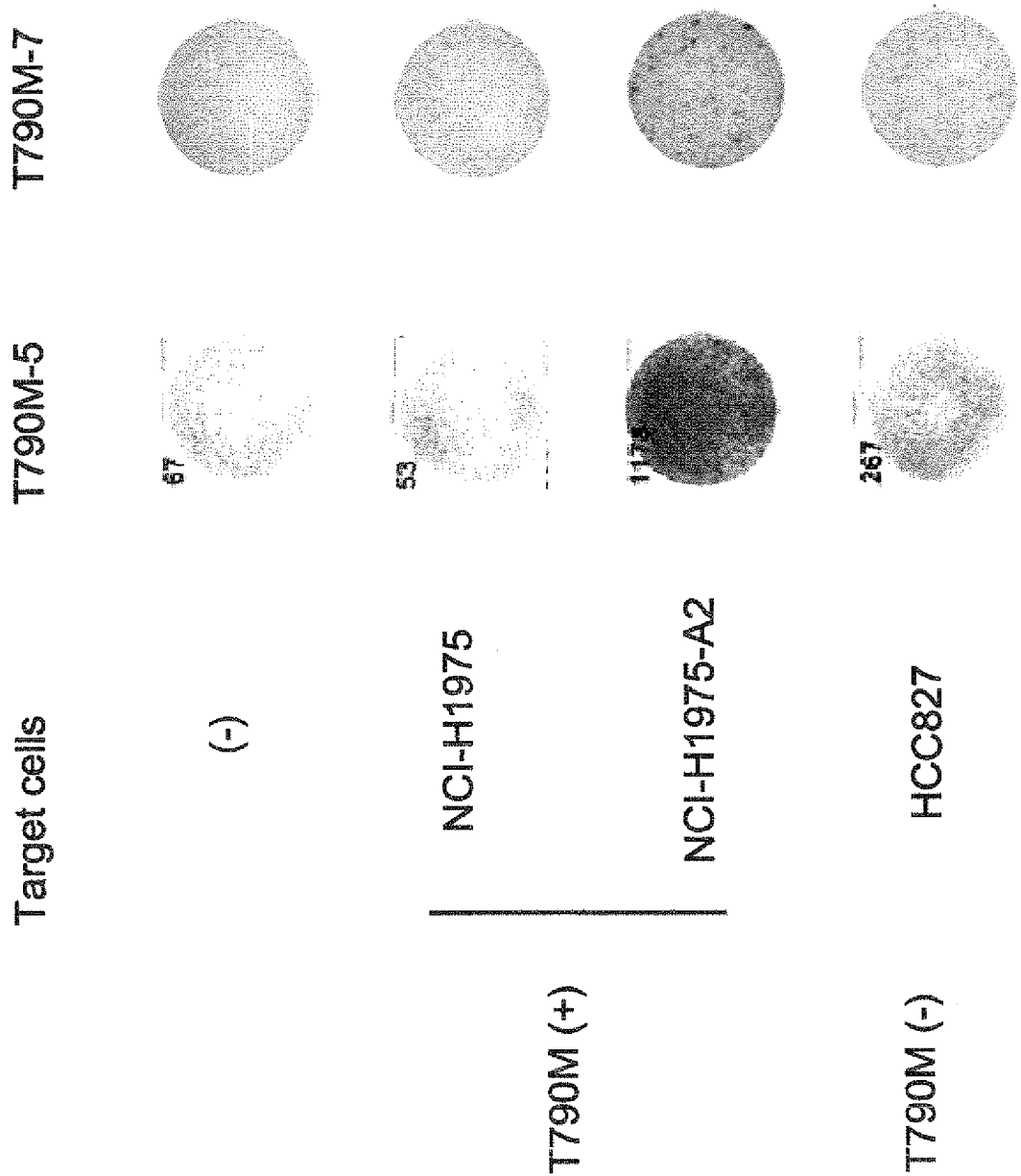
FIG. 2. Reactivity of T790M-5- or T790M-7-stimulated T cells against non-small cell lung cancer (NSCLC) cells having the EGFR T790M mutation. PBMCs from an HLA-A2$^+$ healthy donor were stimulated 5 times with T790M-5 or T790M-7 peptide (10 μg/ml) every 3 or 4 days. CD8$^+$ T cells (2×10$^4$ cells/well) that were isolated from the stimulated PBMCs by using anti-CD8 beads were examined for their reactivity against different NSCLC cell lines, NCI-H1975 (HLA-A2$^-$ T790M$^+$), NCI-H1975-A2 (HLA-A2$^+$ T790M$^+$), and HCC827 (HLA-A2$^-$ T790M), by IFN-γ ELISPOT assay.
Figure 3:
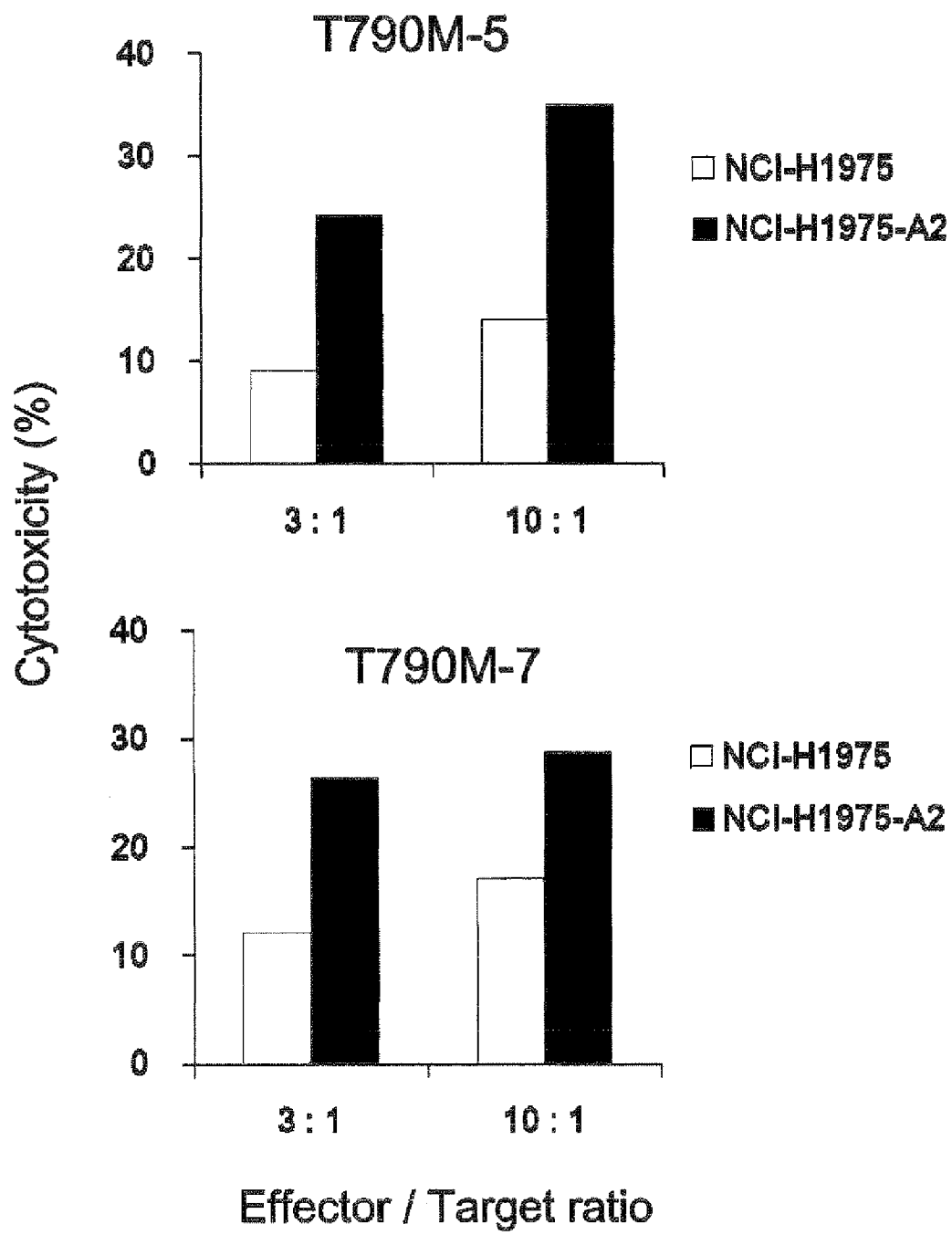
FIG. 3. Cytotoxicity of T790M-5- or T790M-7-stimulated T cells against NSCLC cell lines having the EGFR T790M mutation. PBMCs from an HLA-A2$^+$ healthy donor were stimulated 5 times with T790M-5 or T790M-7 peptide (10 μ/ml) every 3 or 4 days. The stimulated PBMCs were examined for their cytotoxicity against NSCLC cell lines (NCI-H1975 (HLA-A2 T790M$^+$) and NCI-H1975-A2 (HLA-A2$^+$ T790M$^{+))}$ (2×10$^3$ cells/well), at the indicated effector/target ratios. The cytotoxicity was calculated as follows: cytotoxicity (%)=[(test release−spontaneous release)/(maximal release−spontaneous release)]×100.
Figure 4:
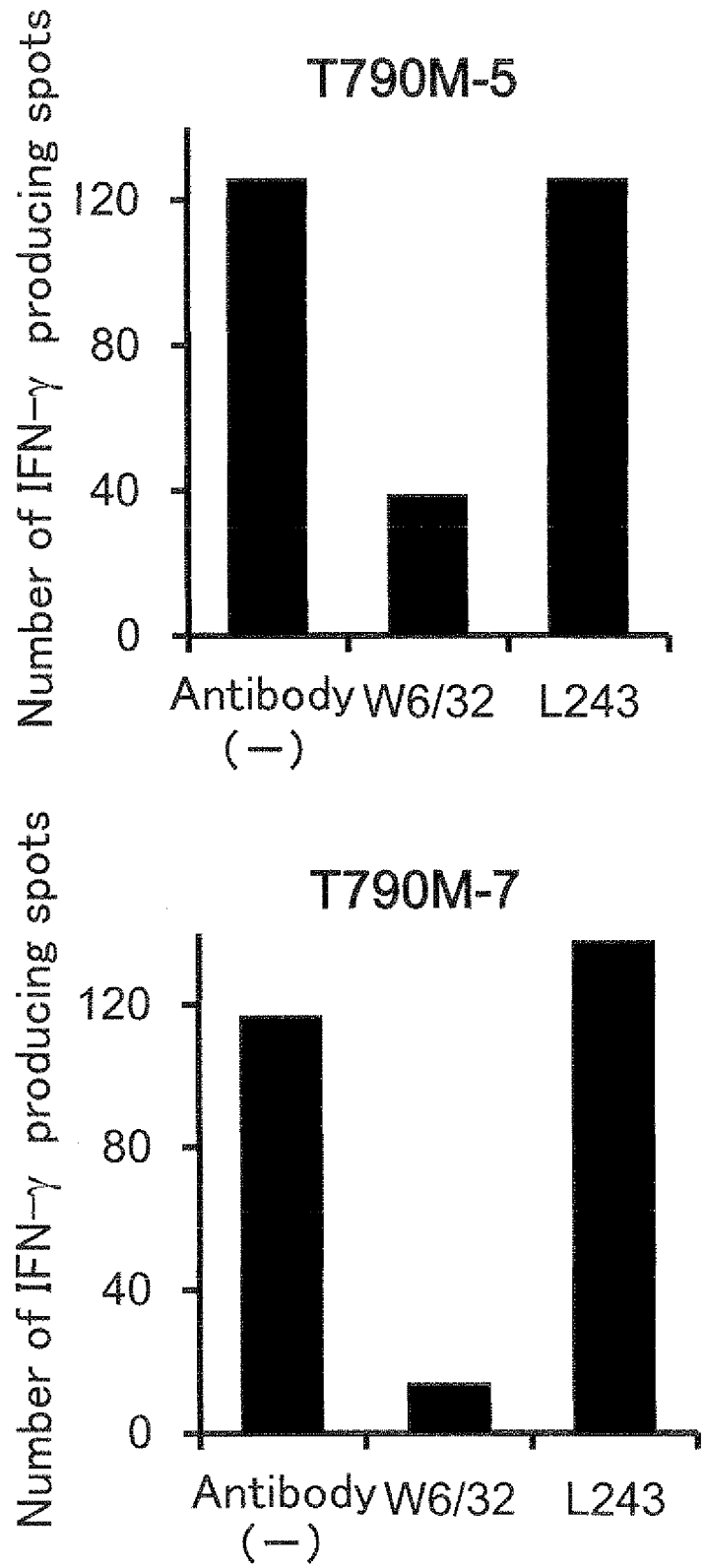
FIG. 4. HLA class I-restricted reactivity of T790M-5- or T790M-7-stimulated T cells against NSCLC cell lines having the EGFR T790M mutation. PBMCs from an HLA-A2$^+$ healthy donor were stimulated 5 times with T790M-5 or T790M-7 peptide (10 μg/ml) every 3 or 4 days. The stimulated PBMCs were examined for their reactivity against NCI-H1975-A2 (HLA-A2$^+$ T790M$^+$) in the presence of anti-HLA class I (W6/32) or anti-HLA class II (L243) antibody by IFN-γ ELISPOT assay.

(4) Reactivity of Peptide-Stimulated T Cells Against NSCLC Cells Having the EGFR T790M Mutation CD8$^+$ T cells purified from the PBMCs after repeated stimulation with T790M-5 or T790M-7 were examined for their reactivity against NSCLC cell lines (NCI-H1975 (HLA-A2$^-$ T790M$^+$), NCI-H1975-A2 (HLA-A2$^+$ T790M$^+$), and HCC827 (HLA-A2$^-$ T790M$^-$)) by IFN-γ ELISPOT assay. As shown in FIG. 2, the T790M-5-stimulated CD8$^+$ T cells as well as the T790M-7-stimulated CD8$^+$ T cells showed a significant IFN-γ production in response to NCI- H1975-A2, but not to HLA-A2-negative parental NCI-H1975 cells. In addition, the T790M-5-stimulated CD8+ T cells and the T790M-7-stimulated CD8+ T cells showed no responses against an EGFR/T790M-negative cell line, HCC827. Moreover, the T790M-5-stimulated PBMCs and the T790M-7-stimulated PBMCs showed substantial cytotoxicity against NCI-H1975-A2, but not against HLA-A2-negative NCI-H1975 cells (FIG. 3). Further, PBMCs after repeated stimulation with T790M-5 or T790M-7 were examined for their reactivity against NCI-H1975-A2 (HLA-A2+ T790M+) in the presence of anti-HLA class I (W6/32) or anti-HLA class II (L243) antibody by IFN-γ ELISPOT assay. As shown in FIG. 4, the T790M-5-stimulated PBMCs and the T790M-7-stimulated PBMCs showed a significant IFN-γ production in response to NCI-H1975-A2 in the absence of the antibody or in the presence of the anti-HLA class II (L243) antibody. In contrast, the IFN-γ production reduced in the presence of the anti-HLA class I (W6/32) antibody. Those results suggests that the T790M-5 and T790M-7 epitopes are expressed on the cell surface of NSCLC cells having the EGFR T790M mutation in an MHC class I-restricted manner.

(5) Cross Reactivity of T790M-5-Stimulated T Cells to a Wild-Type Peptide

Figure 5:
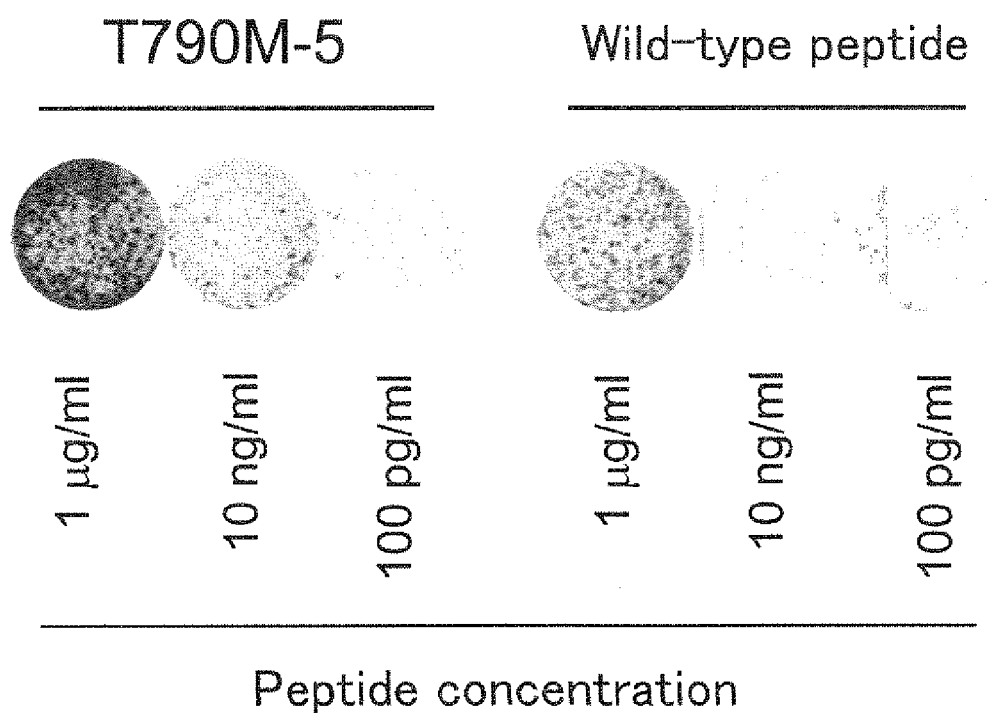
FIG. 5. Cross reactivity of T790M-5-stimulated T cells to a wild-type peptide. PBMCs from an HLA-A2$^+$ healthy donor were stimulated 5 times with T790M-5 (10 μg/ml) every 3 or 4 days. The stimulated PBMCs were examined for their reactivity to T790M-5 or a wild-type peptide by IFN-γ ELISPOT assay.

PBMCs after repeated stimulation with T790M-5 were examined for their reactivity against a wild-type peptide (TQLMPFGCLL) (SEQ ID NO: 12) by IFN-γ ELISPOT assay. As shown in FIG. 5, the T790M-5-stimulated PBMCs responded to a high concentration (1 μg/ml), but not to a low concentration (10 ng/ml), of the wild-type peptide. In contrast, the T790M-5-stimulated PBMCs responded to T790M-5 even at a low concentration (10 ng/ml). Since the T790M-5-stimulated T cells showed a low reactivity to the wild-type peptide, the cells were considered to show a low reactivity to normal cells expressing the wild-type peptide. Those results indicate that T790M-5 is less likely to induce a response to normal cells expressing a wild-type peptide, that is, an autoimmune response, when administered to a living body as a vaccine antigen.

(6) Immunogenicity of T790M-5 and T790M-7 in Blood of HLA-A2+ Lung Cancer Patients For evaluation of immunogenicity of T790M-5 and T790M-7 in blood of lung cancer patients, PBMCs of 17 HLA-A2+ lung cancer patients were repeatedly stimulated with T790M-5 or T790M-7 and examined for their ability to induce peptide-specific CTLs by IFN-γ ELISPOT assay. The peptide-specific CTLs were induced in 3 of 6 gefitinib-sensitive patients (50%) and in 2 of 11 gefitinib-resistant patients (18%) (Table 2). Those results suggest that T790M-specific T cells have disappeared in gefitinib-resistant patients and this destroys the immunosurveillance system and allows the appearance of cancer cells having T790M mutation. Therefore, the appearance of the EGFR tyrosine kinase inhibitor resistant-mutation (T790M) is expected to be prevented in lung cancer patients receiving gefitinib by the immunotherapy with T790M-5 or T790M-7 that could maintain the immunosurveillance system.

TABLE 2

Immunogenicity of T790M-5 and T790M-7 in blood of HLA-A2+ lung cancer patients.

| Case No. | Age | Sex | T790M-5 | T790M-7 |
|---|---|---|---|---|
| Gefitinib-sensitive patients | | | | |
| 1 | 59 | M | +* | + |
| 2 | 60 | M | −** | − |
| 3 | 77 | F | + | − |
| 4 | 65 | F | − | − |
| 5 | 64 | F | − | − |
| 6 | 67 | F | + | − |
| Gefitinib-resistant patients | | | | |
| 1 | 60 | F | − | − |
| 2 | 60 | M | − | − |
| 3 | 81 | M | − | − |
| 4 | 78 | F | − | − |
| 5 | 57 | F | − | − |
| 6 | 76 | F | − | − |
| 7 | 79 | F | − | − |
| 8 | 74 | M | − | − |
| 9 | 68 | F | + | − |
| 10 | 59 | M | + | − |
| 11 | 59 | M | − | − |

*+, responsive to T790M-5 or T790M-7.
**−, not responsive to T790M-5 or T790M-7.
M, male; F, female.

EXAMPLE 2

1. Materials and Methods

(1) Mice

HLA-A2 transgenic (Tg) mice (HHD, H-2D$^{b-/-}$β2m$^{-/-}$) were provided from Prof. Matsui of Saitama Medical University and maintained in the animal facility of National Cancer Center Hospital East.

(2) Peptides and Cell Lines

The peptides comprising the mutated residue at position 790 (T790M) of EGFR were obtained from SCRUM Inc (Tokyo, Japan) (purity>95%). The control HLA-A2-restricted peptides, HIV$_{77-85}$-derived peptide (SLYNTVATL) (SEQ ID NO: 10) and CMV$_{495-503}$ peptide (NLVPMVATV) (SEQ ID NO: 13), were obtained from American Peptide Co. (Sunnyvale, Calif., U.S.). H-2K$^b$-restricted OVA$_{257-264}$ peptide (SIINFEKL) (SEQ ID NO: 14) was obtained from AnaSpec (Fremont, Calif., USA) (purity>95%). NSCLC cell lines, NCI-H1975 and NCI-H1975-A2 cells were provided from Prof. Yano of Kanazawa university and Prof. Sasada of Kurume university, respectively. An artificial antigen presenting cell (aAPC: K562/HLA-A2/CD80/CD83) was provided from Dr. Hirano of Dana-Farber Cancer Institute. RMA-S-HHD was provided from Prof. Matsui of Saitama Medical University. These cell lines were maintained in RPMI 1640 medium (Sigma Chemical Company, St. Louis, Mo., USA) supplemented with 10% heat inactivated fetal bovine serum (FES), 100 μg/ml streptomycin, and 100 IU/ml penicillin.

(3) Prediction of EGFR-T790M-Derived HLA-A2-Binding Peptides

BIMAS (http://www-bimas.cit.nih.gov/molbio/hla_bind) was employed to predict 9-mer or 10-mer HLA-A2 binding peptides from EGFR-T790M. Peptides that showed better scores by the prediction server and modified peptides thereof were selected for evaluation.

(4) HLA Class I Stabilization Assay

The binding of predicted peptides to an HLA-A2 molecule was evaluated by HLA class I stabilization assay with TAP2-deficient T2 cells (HLA-A2+) (RIKEN, Saitama, Japan). After overnight culture in RPMI 1640 medium at 26° C., T2 cells were cultured for 3 hours at 26° C. in the presence of each synthetic peptide. The cells were cultured for 2.5 hours at 37° C., and then stained with anti-HLA-A2 antibody (BB7.2) (MBL, Nagoya, Japan), followed by analysis with flow cytometry. The binding capability of each peptide to the HLA-A2 molecule was evaluated by comparing the mean fluorescence intensity (MFI) of HLA-A2 expression of the peptide with those of the positive and the negative controls. The HLA-A2-restricted HIV peptide and CMV peptide were used as positive controls, and H-2K$^b$-restricted OVA peptide was used as a negative control.

(5) Preparation of Mouse Dendritic Cells

Bone-marrow cells were obtained by hemolysis of cells in whole bone marrow collected from an HLA-A2Tg mouse. The bone-marrow cells (4×10$^6$ cells) were cultured for 1 week in RPMI medium in the presence of mouse GM-CSF and 2ME to provide mouse bone marrow-derived dendritic cells. The dendritic cells thus obtained were stained with anti I-A$^b$, CD11c, CD14, CD40, and CD86 antibodies (BioLegend, San Diego, Calif., USA) to confirm the differentiation to dendritic cells by flow cytometry.

(6) Determination of Immunogenicity in Mouse

Mouse dendritic cells were loaded with each peptide (10 μg/ml). For immunization, the dendritic cells (5×10$^5$ cells) suspended in 200 μl PBS were intraperitoneally-injected into an HLA-A2Tg mouse (8-10 weeks old) on Day 0 and Day 7. On Day 14, the spleen was collected from the mouse. CD8$^+$ cells isolated from the spleen with microbeads (Miltenyi Biotec, Bergisch Gladbach, Germany) were examined for induction of peptide-specific CTLs by IFN-γ ELISPOT assay.

(7) Preparation of Human Dendritic Cells

Peripheral blood was obtained with written informed consent from HLA-A2 healthy donors. HLA-A2 expression was confirmed by genetic typing in Mitsubishi Chemical Medience Corporation. PBMCs were purified from the peripheral blood by Ficoll-Paque (General Electric Healthcare Bio-Sciences, Uppsala, Sweden) density centrifugation and CD14$^+$ cells were isolated with microbeads. The CD14$^+$ cells were cultured in RPIM medium in the presence of GM-CSF and IL-4 for 5 days, further cultured with TNF-α and PGE2 for differentiation into mature dendritic cells, and used on Day 7. The differentiation into mature dendritic cells was confirmed with anti HLA-DR antibody (Becton-Dickinson Co., Sunnyvale, Calif., USA), and anti CD11c, CD14, CD40, CD80, CD83, and CD86 antibodies (BD Biosciences, San Jose, Calif., USA).

(8) Generation of Antigen-Specific T Cells

CD8$^+$ cells were isolated from PBMCs of HLA-A2$^+$ healthy donors with microbeads. The CD8$^+$ cells (2×10$^6$ cells) were co-cultured with dendritic cells that were loaded with each peptide (10 μg/ml) and irradiated with 100 Gy in 2 ml RPMI medium containing 10% AB serum (SIGMA). On Days 7 and 14, aAPCs that were loaded with each peptide (10 μg/ml) and irradiated with 200 Gy were added to the culture. On Days 3, 10, and 17, IL-2 (10 IU/ml) and IL-15 (10 ng/ml) were added to the culture medium. On Day 21, the cultured cells were collected, and CD8$^+$ cells were isolated with microbeads for further experiments.

(9) Immune Assays

The peptide-specific immune response was evaluated by IFN-γ ELISPOT assay. The mouse or human CD8$^+$ cells as described in (6) or (8) above (1×10$^5$ cells/well) were cultured with RMA-S-HHD or T2 cells (1×10$^5$ cells/well) that were loaded with a peptide (10 μg/ml) for 20 hours at 37° C. in 96-well ELISPOT plate coated with anti-human IFN-γ antibody. After washing, the spots were developed with biotin-conjugated anti IFN-γ mAb, streptavidin-HRP, and AEC substrate. The spot numbers were then counted by Eliphoto system (Minerva Tech, Tokyo, Japan). The induction of peptide specific CTLs against NCI-H1975 and NCI-H1975-A2 was also examined. The number of cells and concentration of the pulsed peptide were modified in some experiments.

(10) CD107a Assay and Establishment of Peptide-Specific CTL Line

The CD8$^+$ cells as described in (8) above were cultured with target cells (peptide-loaded T2 or NCI-H1975-A2) at a effector/target ratio 2:1 in the presence of anti-CD107a antibody (BD Biosciences) for 3.5 hours at 37° C. and analyzed by a flow cytometer. CD8$^+$CD107a$^+$ cells were sorted by a cell sorter as peptide-specific CTLs to a 96-well plate (1-100 cells/well). The sorted peptide-specific CTLs were cultured with allo PBMCs irradiated with 100 Gy (8×10$^4$ cells), which were used as feeder cells, for 14-21 days in AIM-V medium (Gibco, Carlsbad, Calif., USA) containing 10% AB serum, IL-2 (200 U/mL) and phytohemagglutinin-P (PHA) (5 μg/mL) to establish a peptide-specific CTL line. The peptide specificity of the established CTL line was confirmed by IFN-γ ELISPOT assay.

(11) Cytotoxicity Assay

Cytotoxicity of peptide-specific CTLs was examined by an assay with Calcein labeling. Target cells (NCI-H1975 or NCI-H1975-A2) were labeled with Calcein AM (Dojindo, Kumamoto, Japan). The target cells (1×10$^4$ cells) were co-cultured with effector cells at the following effector/target ratio for 4-6 hours in 96-well half plate (Corning, N.Y., USA). Cytotoxicity was determined with Terascan VPC system (Minerva Tech). The effector/target ratio was 3:1 or 10:1. The cytotoxicity was calculated as follows: cytotoxicity (%)=[(test release−spontaneous release)/(maximal release−spontaneous release)]×100.

2. Results (1) Prediction of EGFR-T790M-Derived HLA-A2-Binding Peptides

Peptides (9 to 10-mer) that would bind to an HLA-A2 molecule with higher probability were predicted by BIMAS server. Three peptides, T790M-A, T790M-B, and T790M-C, each of which showed a good score higher than that of the corresponding wild-type peptide lacking T790M mutation, were selected. Further, modified peptides were prepared by alteration of an anchor residue that was important for HLA binding such that the binding capability was increased. Five peptides, including two modified peptides comprising one amino acid alteration (T790M-D and T790M-E), were examined as candidates (Table 3).

TABLE 3

Candidate peptides predicted as HLA-A2-binding peptides.

| Peptide | Amino acid sequence | BIMAS score (wild-type) |
|---|---|---|
| T790M-A | IMQLMPFGC (SEQ ID NO: 15) | 35.378 (0.68) |
| T790M-B | MQLMPFGCLL (SEQ ID NO: 5) | 51.77 (30.453) |
| T790M-C | LIMQLMPFGC (SEQ ID NO: 3) | 24.921 (6.735) |
| T790M-D | IMQLMPFGV (SEQ ID NO: 16) | 495.288 |
| T790M-E | IMQLMPFGL (SEQ ID NO: 17) | 152.124 |

(2) HLA-A2-Binding Capability of EGFR-T790M-Derived Peptides

Figure 6:
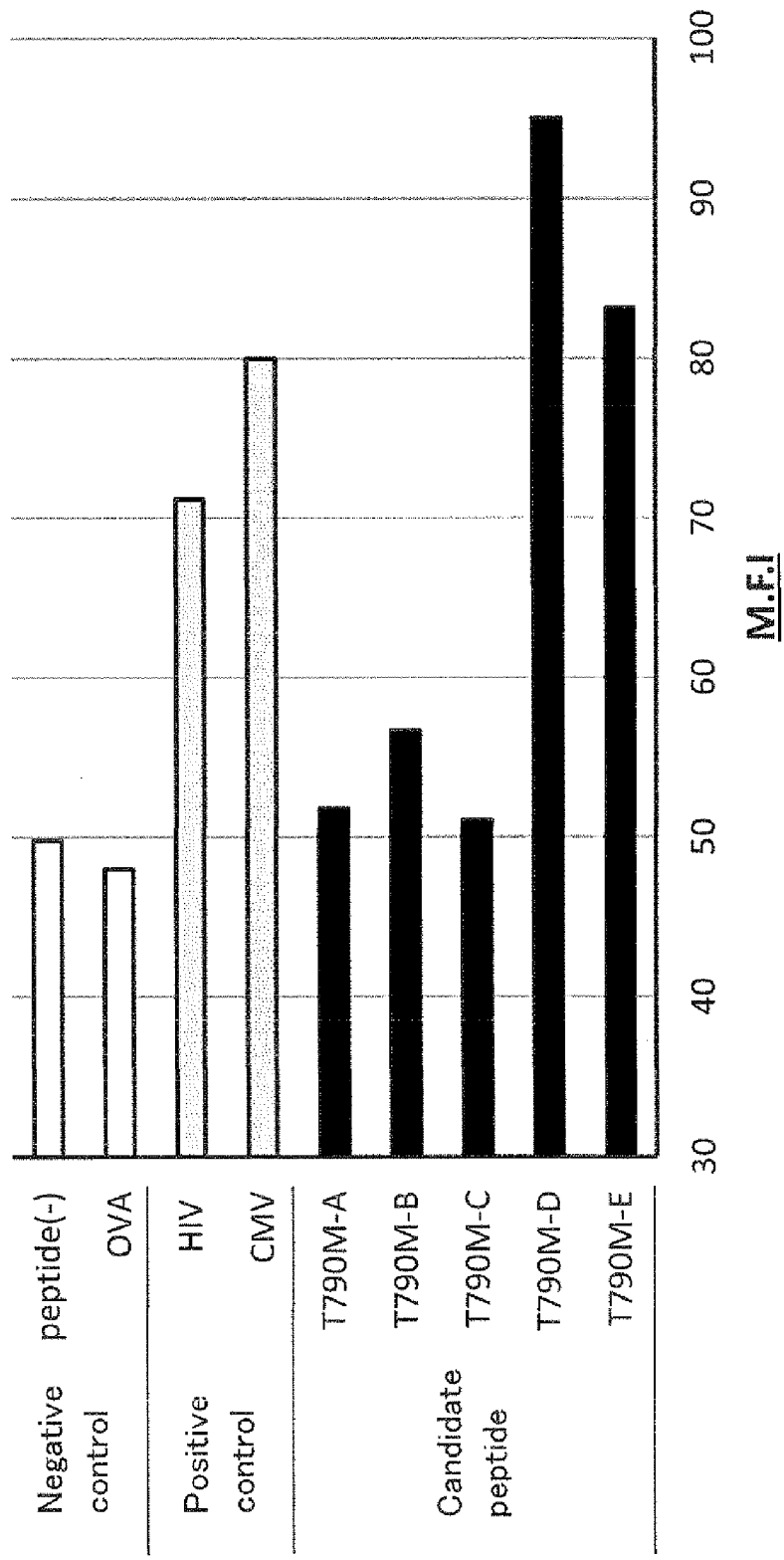
FIG. 6. HLA-A2-binding capability of EGFR-T790M-derived peptides. The binding of selected peptides to an HLA-A2 molecule was evaluated by HLA class I stabilization assay with TAP2-deficient T2 cells expressing HLA-A2.

The HLA-A2-binding capability of the selected peptides was confirmed by cell surface HLA class I stabilization assay with TAP-deficient cell line T2 expressing HLA-A2. As shown in FIG. 6, T790M-A, T790M-B, and T790M-C were confirmed to bind to HLA-A2. The modified peptides T790M-D and T790M-E showed a higher binding.

(3) Immunogenicity of EGFR-T790M-Derived Candidate Peptides in HLA-A2Tg Mice

Figure 7:
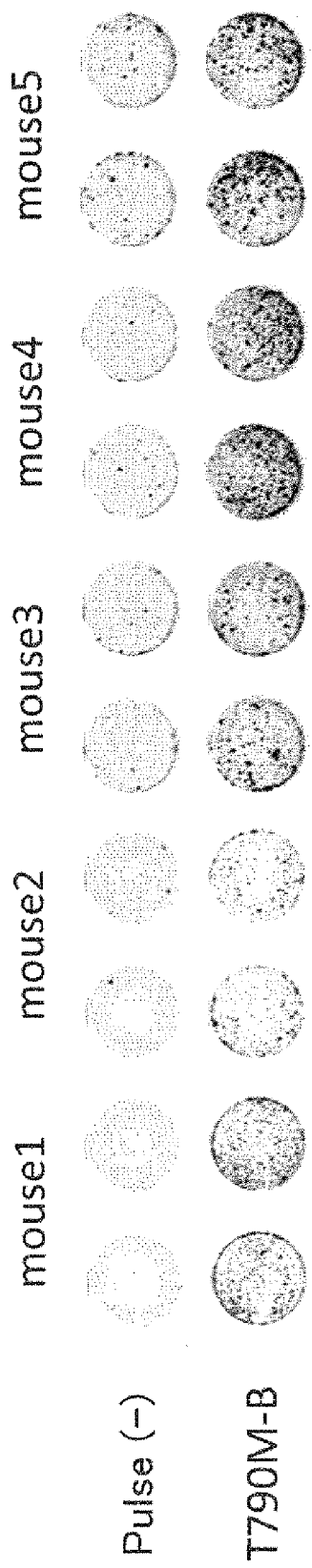
FIG. 7. Immunogenicity of EGFR-T790M-derived candidate peptides in HLA-A2Tg mice. Immunogenicity of candidate peptides in HLA-A2Tg mice was examined by vaccination of dendritic cells. The result of T790M-B is shown.

Immunogenicity of the candidate peptides in HLA-A2Tg mice was examined by vaccination of dendritic cells. Dendritic cells were induced from bone marrow of an HLA-A2Tg mouse and loaded with each of the candidate peptides. The dendritic cells were intraperitoneally-injected into the HLA-A2Tg mouse twice for immunization. From the immunized mouse, the spleen was collected and examined by IFN-γ ELISPOT assay. As shown in FIG. 7, T790M-B-specific CTLs were induced in all of the five immunized mice. For other four peptides, no peptide-specific CTL was induced.

Figure 8:
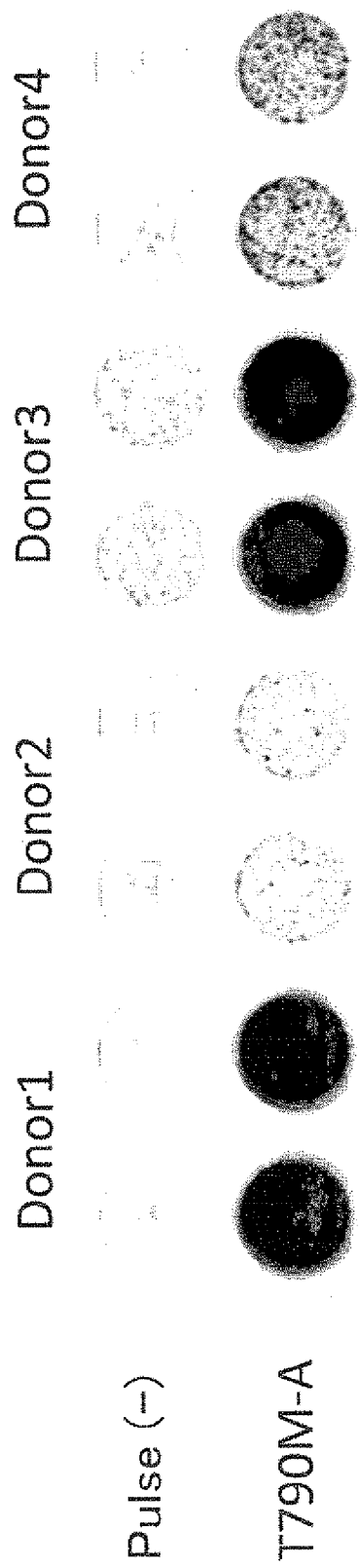
FIG. 8. Immunogenicity of EGFR-T790M-derived candidate peptides in PBMCs from healthy donors. For evaluation of immunogenicity of candidate peptides, induction of peptide-specific CTLs from PBMCs of HLA-A2⁺ healthy donors was examined. The result of T790M-A is shown.

(4) Immunogenicity of EGFR-T790M-Derived Candidate Peptides in PBMCs from Healthy Donors For evaluation of immunogenicity of the EGFR-T790M-derived candidate peptides, induction of peptide-specific CTLs from PBMCs of HLA-A2$^+$ healthy donors was examined. CD8$^+$ T cells were isolated and stimulated with peptide-loaded dendritic cells and aAPCs. T790M-A-specific CTLs were induced in all of 4 donors examined (FIG. 8). Similarly, T790M-B-specific CTLs were induced in 2 of 4 donors examined. For other three peptides, no peptide-specific CTL was induced. Then, from the T790M-A-specific CTLs thus induced, CD8$^+$CD107a$^+$ cells were sorted by CD107a assay to establish a T790M-A-specific CTL line.

Figure 9:
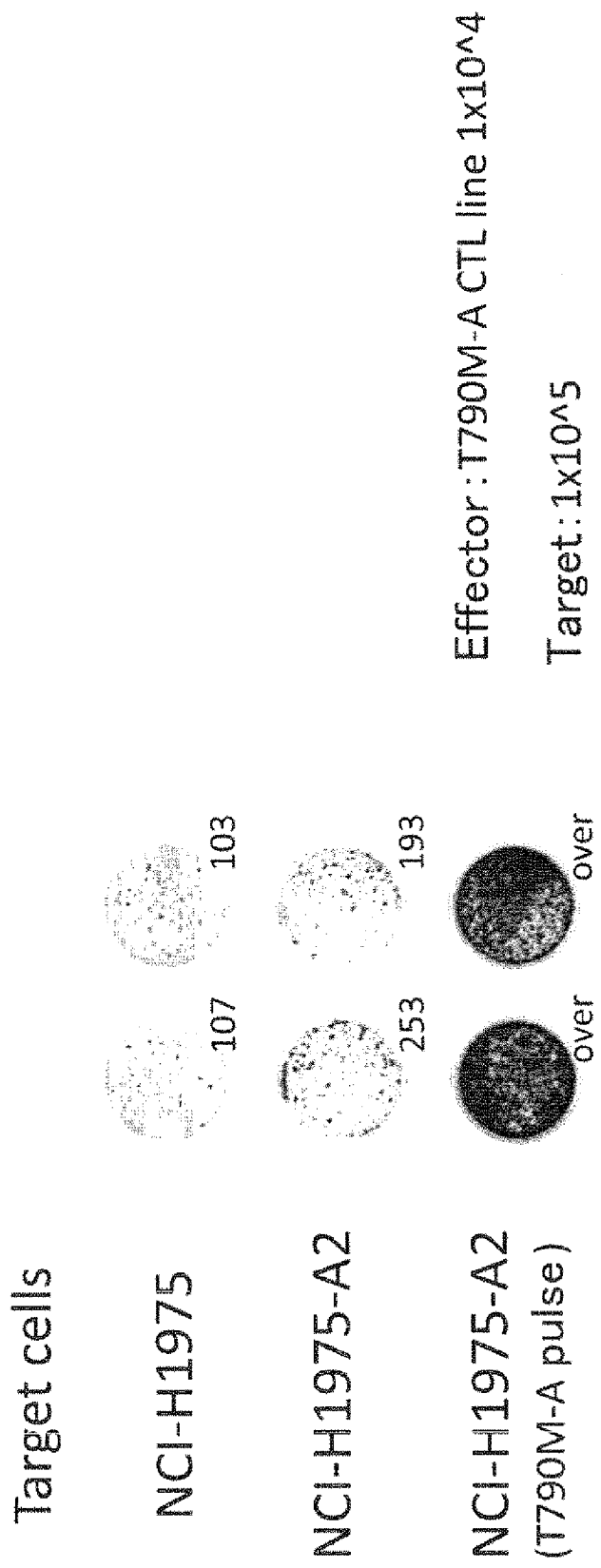
FIG. 9. Reactivity of T790M-A-specific CTL line against NSCLC cell lines having the EGFR T790M mutation (1). The established T790M-A-specific CTL line was examined for reactivity against NSCLC cell lines (NCI-H1975 (HLA-A2⁻ T790M⁺) and NCI-H1975-A2 (HLA-A2⁺ T790M⁺)) by IFN-γ ELISPOT assay.
Figure 10:
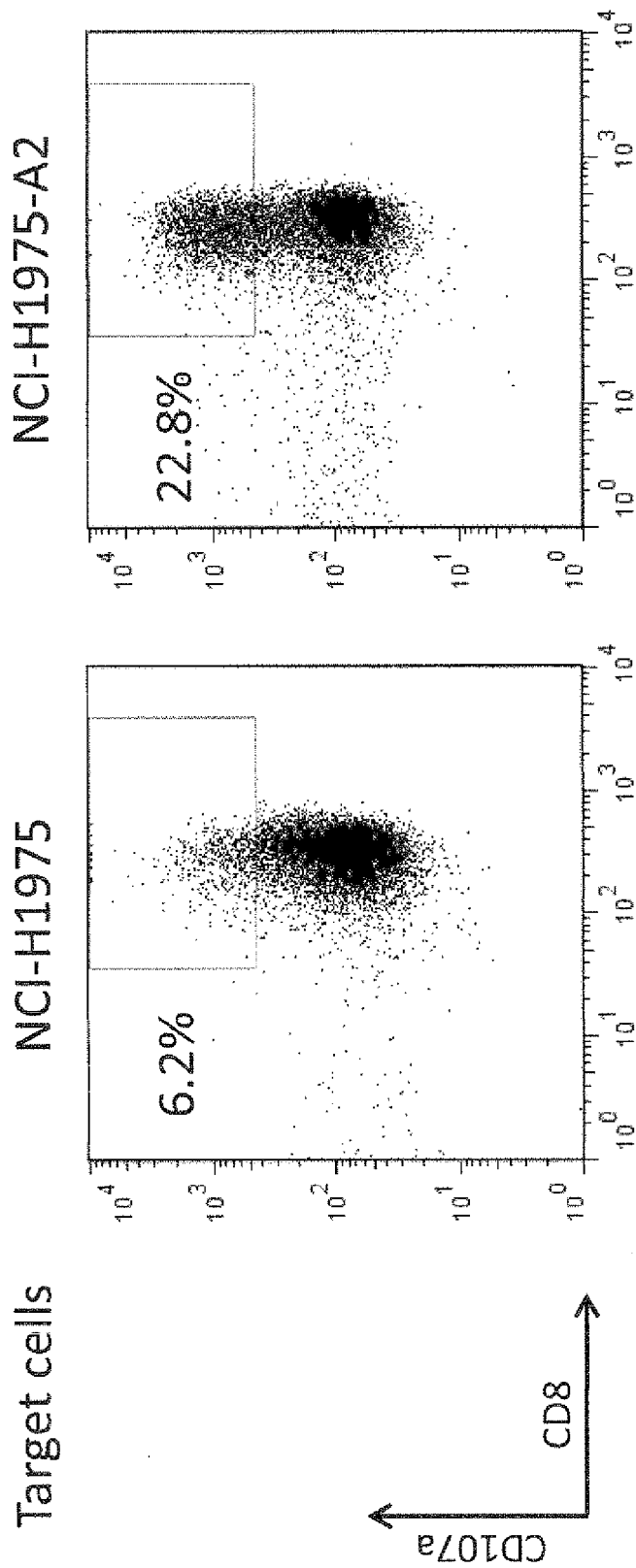
FIG. 10. Reactivity of T790M-A-specific CTL line against NSCLC cell lines having the EGFR T790M mutation (2). The established T790M-A-specific CTL line was examined for reactivity against NSCLC cell lines (NCI-H1975 (HLA-A2⁻ T790⁺) and NCI-H1975-A2 (HLA-A2⁺ T790M⁺)) by CD107a assay.
Figure 11:
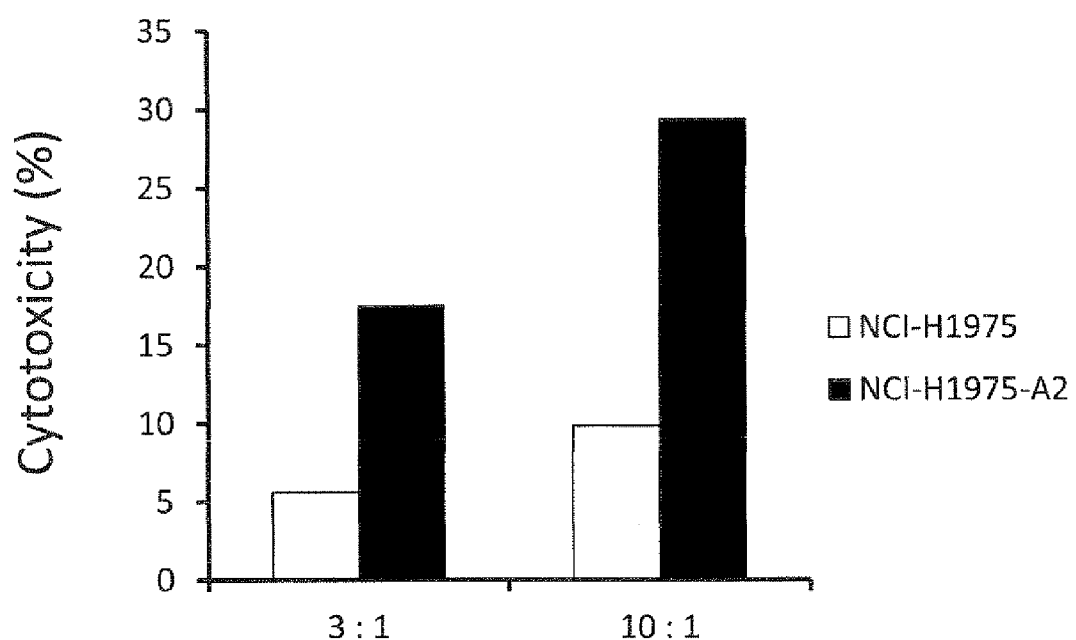
FIG. 11. Reactivity of T790M-A-specific CTL line against NSCLC cell lines having the EGFR T790M mutation (3). The established T790M-A-specific CTL line was examined for cytotoxicity against NSCLC cell lines (NCI-H1975 (HLA-A2⁻ T790M⁺) and NCI-H1975-A2 (HLA-A2⁺ T790M⁺)).

(5) Reactivity of T790M-A-Specific CTL Line Against NSCLC Cell Lines Having the EGFR T790M Mutation The established T790M-A-specific CTL line was examined for reactivity against NSCLC cell lines (NCI-H1975 (HLA-A2$^-$ T790M$^+$) and NCI-H1975-A2 (HLA-A2$^+$ T790M$^+$)) by IFN-γ ELISPOT assay and CD107a assay. The CTL line showed a higher IFN-γ production against NCI-H1975-A2 than against HLA-A2-negative NCI-H1975 (FIG. 9). The CD107a assay also detected many CD107a-positive cells in the co-culture with NCI-H1975-A2 (FIG. 10). In addition, the T790M-A-specific CTL line showed cytotoxicity against NCI-H1975-A2, but not against HLA-A2-negative NCI-H1975 cells (FIG. 11). Those results suggest that CTLs recognize the 9-mer peptide, T790M-A, endogenously presented on NCI-H1975-A2 cells to kill the cells.

SEQUENCE FREE TEXT

SEQ ID NO: 1: Synthetic peptide
SEQ ID NO: 2: Synthetic peptide
SEQ ID NO: 3: Synthetic peptide
SEQ ID NO: 4: Synthetic peptide
SEQ ID NO: 5: Synthetic peptide
SEQ ID NO: 6: Synthetic peptide
SEQ ID NO: 7: Synthetic peptide
SEQ ID NO: 8: Synthetic peptide
SEQ ID NO: 9: Synthetic peptide
SEQ ID NO: 10: Synthetic peptide
SEQ ID NO: 11: Synthetic peptide
SEQ ID NO: 12: Synthetic peptide
SEQ ID NO: 13: Synthetic peptide
SEQ ID NO: 14: Synthetic peptide
SEQ ID NO: 15: Synthetic peptide
SEQ ID NO: 16: Synthetic peptide
SEQ ID NO: 17: Synthetic peptide

The invention claimed is:

1. A method of treating cancer by inducing peptide-specific cytotoxic T lymphocytes (CTLs), comprising administering a peptide consisting of the amino acid sequence of SEQ ID NO: 5, 7 or 15 to a patient in need thereof.

2. The method according to claim 1, wherein the peptide consists of the amino acid sequence of SEQ ID NO: 5.

3. The method according to claim 1, wherein the peptide consists of the amino acid sequence of SEQ ID NO: 7.

4. The method according to claim 1, wherein the peptide consists of the amino acid sequence of SEQ ID NO: 15.

5. The method according to claim 1, wherein the peptide is administered intradermally or subcutaneously.

6. The method according to claim 1, wherein the peptide is administered with an incomplete Freund's adjuvant, a polysaccharide, or an immunopotentiating agent.

7. The method according to claim 1, wherein the peptide is administered with incomplete Freund's adjuvant ISA-51, pullulan, complete Freund's adjuvant, Bacillus Calmette-Guérin (BCG), Alum, Granulocyte-macrophage colony-stimulating factor (GM-CSF), interleukin-2 (IL-2), or CpG.

8. The method according to claim 1, wherein from 0.0001 mg to 1000 mg of the peptide is administered.

9. The method according to claim 1, wherein the peptide is administered in a liposome.

10. The method according to claim 1, wherein the peptide is bound to a lipid.

* * * * *